United States Patent
Mucke et al.

(10) Patent No.: US 6,175,057 B1
(45) Date of Patent: Jan. 16, 2001

(54) TRANSGENIC MOUSE MODEL OF ALZHEIMER'S DISEASE AND CEREBRAL AMYLOID ANGIOPATHY

(75) Inventors: Lennart Mucke, Foster City; Tony Wyss-Coray, Berkeley; Eliezer Masliah, Chula Vista, all of CA (US)

(73) Assignee: The Regents of the University of California, Oakland, CA (US)

( * ) Notice: Under 35 U.S.C. 154(b), the term of this patent shall be extended for 0 days.

(21) Appl. No.: 08/947,295

(22) Filed: Oct. 8, 1997

(51) Int. Cl.⁷ .................. A01K 67/00; A01K 67/033; G01N 33/00
(52) U.S. Cl. .................. 800/12; 800/3; 800/18; 424/9.2
(58) Field of Search .................. 800/3, 8, 9, 12, 800/13, 18; 424/9.2

(56) References Cited

U.S. PATENT DOCUMENTS

| | | | |
|---|---|---|---|
| 5,387,742 | 2/1995 | Cordell | 800/2 |
| 5,547,841 | 8/1996 | Marotta et al. | 435/6 |
| 5,604,131 | 2/1997 | Wadsworth et al. | 435/320.1 |
| 5,612,486 | 3/1997 | McConlogue et al. | 800/2 |

FOREIGN PATENT DOCUMENTS

| | | | |
|---|---|---|---|
| WO 95/11994 | 5/1995 | (WO) | C12Q/1/68 |
| WO 96/40895 | 12/1996 | (WO) | C12N/15/00 |
| WO 96/40896 | 12/1996 | (WO) | C12N/15/00 |

OTHER PUBLICATIONS (Mullins et al (1993) Hypertension 22, 630–633.*
Kappell et al (1992) Current Opinion in Biotechnology 3, 548–553.*
Wall (1996) Theriogenology 45, 57–68.*
Houdebine (1994) J. Biotech. 34, 269–287.*
Mullins et al (1996) Journal of Clinical Investigation 98, S37–S40.*
Lannfelt et al (1993) Behav. Brain Res. 57, 207–213.*
Duff (1997) TINS 7, 279–280.*
Brockenstein et al (1995) J. Biol. Chem. 270, 28257–28267.*
Wyss–Coray et al (1995) Am. J. Path. 147, 53–67.*
Monnig et al (1994) FEBS Letters 342, 267–272.*
Games et al (1995) Nature 373, 523–527.*
Lippa, C.F., et al., "Transforming growth factor–beta: neuronal and glial expression in CNS degenerative diseases" *Neurodegeneration* 4(4):425–32(Dec. 1995).
Mattson, M.P., et al., "Cellular signaling roles of TGF beta, TNF alpha and beta APP in brain injury responses and Alzheimer's disease" *Brain Res. Rev.* 23(1–2):47–61(Feb. 23, 1997).
Mazur–Kolecka, B., et al., "Factors produced by macrophages reduce accumulation of Alzheimer's beta–amyloid protein in vascular smooth muscle cells" *Brain Res.* 760(1–2):255–60(Jun. 20, 1997).

Peress, N.S., et al., "Differential expression of TGF–beta 1, 2 and 3 isotypes in Alzheimer's diseases: a comparitive immunohistochemical study with cerebral infarction, aged human and mouse control brains" *J Neuropathol Exp Neurol* 54(6):802–11(Nov. 1995).
Pratt, B.M., et al., "TGF–beta in the central nervous system: potential roles in ischemic injury and neurodegenerative diseases" *Cytokine Growth Factor Rev.* 8(4):267–92(Dec. 1997).
Prehn, J.H., et al., "Protective effect of transforming growth factor–beta 1 on beta–amyloid neurotoxicity in rat hippocampal neurons" *Mol Pharmacol.* 49(2):319–28(Feb. 1996).
Ren, R.F., et al., "Transforming growth factor–beta protects human hNT cells from degeneration induced by beta–amyloid peptide: involvement of the TGF–beta type II receptor" *Mol Brain Res.* 48(2):315–22(Sep. 1997).
Van der Wal, et al., "Transforming growth factor beta 1 is in plaques in Alzheimer and Down pathologies" *Neuroreport*, 4(1):69–72(Jan. 1993).
Verbeek, M.M., et al., "Differences between the pathogenesis of senile plaques and congophilic angiopathy in Alzheimer disease", *J.Neoropathol. Exp. Nruol*, 56(7):751–61 (Jul. 1997).
Wyss–Coray, T., et al., "Amyloidogenic role of cytokine TGF–beta 1 in transgenic mice and in Alzheimer's disease" *Nature* 389(6651):603–6(Oct. 9, 1997).
Wyss–Coray, T., et al., "Increased central nervous system production of extracellular matrix components and development of hydrocephalus in transgenic mice overexpressing transforming growth factor–beta 1" *Am. J. Pathol.* 147(1):53–67(Jul. 1995).
Wyss–Coray et al., "Increased Central Nervous System Production of Extracellular Matrix Components and Development of Hydrocephalus in Transgenic Mice Overexpressing Transforming Growth Factor–$\beta 1$" *American Journal of Pathology* (Jul. 1995) 147(1):53–67.
Rockenstein et al., "Levels and Alternative Splicing of Amyloid $\beta$ Protein Precursor (APP) Transcripts in Brains of APP Transgenic Mice and Humans with Alzheimer's Disease" *J Biol Chem* (Nov. 1995) 270(47):28257–28267.
Games et al., "Alzheimer–type neuropathology in transgenic mice overexpressing V717F $\beta$–amyloid precursor protein" *Nature* (Feb. 1995) 373(6514):523–527.

(List continued on next page.)

*Primary Examiner*—Deborah Crouch
(74) *Attorney, Agent, or Firm*—Carol L. Francis; Paula A. Borden; Bozicevic, Field & Francis LLP

(57) ABSTRACT

The present invention features non-human transgenic animal models for Alzheimer's disease (AD) and CAA, wherein the transgenic animal is characterized by 1) overexpression of bioactive transforming growth factor-$\beta 1$ (TGF-$\beta 1$) or 2) both overexpression of bioactive TGF-$\beta 1$ and expression of a human amyloid $\beta$ precursor protein (APP) gene product. The transgenic animals may be either homozygous or heterozygous for these alterations. Bigenic animals are further characterized by development of AD-associated and/or CAA-associated pathology within about two to three months of age.

23 Claims, 5 Drawing Sheets

OTHER PUBLICATIONS

Masliah et al., "Comparison of Neurodegenerative Pathology in Transgenic Mice Overexpressing V717F β–Amyloid Precursor Protein and Alzheimer's Disease" *J Neurosci* (Sep. 1996) 16(18):5795–5811.

Fillit et al., "Disorders of the Extracellular Matrix and the Pathogenesis of Senile Dementia of the Alzheimer's Type," *Lab Invest* (1995) 72:249–253.

Wisniewski et al., "Ultrastructural Studies of the Cells Forming Amyloid in the Cortical Vessel Wall in Alzheimer's Disease," *Acta Neuropathol* (1992) 84:11–127.

Schmechel et al., "Increased Amyloid β–peptide Deposition in Cerebral Cortex as a Consequence of Apolipoprotein E Genotype in Late–Onset Alzheimer's Disease," *Proc Natl Acad Sci USA* (1993) 90:9649–9653.

Mucke, "In Vivo CNS Effects of Molecules Implicated in Alzheimer's Disease (AD) Pathogenesis" Abstract, Keystone Meeting (Feb. 1997).

Mattson et al., "Cellular signaling roles of TGFβ, TNFα and βAPP in brain injury responses and Alzheimer's diease" *Brain Res Brain Res Rev* (Feb. 1997) 23(1–2):47–61.

Schmitt et al., "The production of an amyloidogenic metabolite of the Alzheimer amyloid beta precursor protein (APP) in thyroid cells is stimulated by interleukin 1 beta, but inhibited by interferon gamma" *J Clin Endocrinol Metab* (Apr. 1996) 81(4):1666–1669.

Chao et al., "Transforming growth factor–beta protects human neurons against beta–amyloid–induced injury" *Mol Chem Neuropathol* (Oct. 1994) 23(2–3):159–178.

Monning et al., "Transforming growth factor beta mediates increase of mature transmembrane amyloid precursor protein in microglial cells" *FEBS Lett* (Apr. 1994) 342(3):267–272.

Gray et al., "Regulation of beta–amyloid precursor protein isoform mRNAs by transforming growth factor–beta 1 and interleukin–1 beta in astrocytes" *Brain Res Mol Brain Res* (Aug. 1993) 19(3):251–256.

Bodmer et al., "Transforming growth factor–beta bound to soluble derivatives of the beta amyloid precursor protein of Alzheimer's disease" *Biochem Biophys Res Commun* (Sep. 1990) 171(2):890–897.

Ren et al., "Transforming growth factor–beta protect primary rat hippocampal neuronal cultures from degeneration induced by beta–amyloid peptide" *Brain Res* (Sep. 1996) 732(1–2):16–24.

Choi–Miura et al., "Relationship between multifunctional protein 'clusterin' and Alzheimer disease" *Neurobiol Aging* (Sep. 1996) 17(5):717–722.

Prehn et al., "Protective effect of transforming growth factor–beta 1 on beta–amyloid neurotoxicity in rat hippocampal neurons" *Mol Pharmacol* (Feb. 1996) 49(2):319–328.

Finch et al., "TGF–beta 1 is an organizer of responses to neurodegeneration" *J Cell Biochem* (Dec. 1993) 53(4):314–322.

Johnson–Wood, et al., "Amyloid r\precursor protein processing and Aβ $_{42}$ deposition in a transgenic mouse model of Alzheimer disease," *Proc Natl Acad Sci USA* (1997) 94:1550–1555.

Chao, C.C., et al., "Serum cytokinc levels in patients with Alzheimer's disease" *Clin Diagn Lab Immunol*, 1(4):433–6(Jul. 1994).

Chao, C.C., et al., "Transforming growth factor beta in Alzheimer's disease" *Clin Diagn Lab Immunol* 1(1):109–10(Jan. 1994).

Duff, K., "Recent work on Alzheimer's disease transgenics" *Curr. Opin. Biotechnol.* 9(6):561–4(Dec. 1998).

Finch, C.E., et al., "TGF–beta 1 is an organizer of responses to neurodegeneration" *J Cell Biochem* 53(4):314–22(Dec. 1993).

Flanders, K.C., et al., "Altered expression of transforming growth factor–beta in Alzheimer's disease" *Neurology* 45(8):1561–9(Aug. 1995).

Flanders, K.C., et al., "Transforming growth factor–betas in neurodegenerative disease" *Prog. Neurobiol.* 54(1):71–85(Jan. 1998).

Frautschy, S.A., et al., "Rodent models of Alzheimer's disease: rat A beta infusion approaches to amyloid deposits" *Neurobiol Aging* 17(2):311–21(Mar.–Apr. 1996).

Harris–White, M.E., et al., "Effects of transforming growth factor–beta (Isoforms 1–3) on amyloid–beta deposition, inflammation, and cell targeting in organotypic hippocampal slice cultures" *J. Neurosci.* 18(24), 10366–74(Dec. 15, 1998).

S. Huang, S.S., et al., "Amyloid beta–peptide possesses a transforming growth factor–beta activity" *J. Biol. Chem.* 273(42):27640–4(Oct. 16, 1998).

* cited by examiner

TRANSGENIC MOUSE MODEL OF ALZHEIMER'S DISEASE AND CEREBRAL AMYLOID ANGIOPATHY

STATEMENT AS TO FEDERALLY SPONSORED RESEARCH

This invention was made, at least in part, with a government grant from the National Institutes of Health (Grant No. AG11385). The U.S. government may have certain rights in this invention.

FIELD OF THE INVENTION

The invention relates generally to the field of non-human, transgenic animal models of conditions associated with accumulation of amyloid polypeptides, particulary Alzheimer's and cerebral amyloid angiopathy (CAA).

BACKGROUND OF THE INVENTION

A number of important neurological diseases including Alzheimer's disease (AD), cerebral amyloid angiopathy (CAA), and prion diseases are characterized by the deposition of aggregated proteins, referred to as amyloid, in the central nervous system (CNS) (for reviews, see Glenner et al. (1989) *J. Neurol. Sci.* 94:1–28; Haan et al. (1990) *Clin. Neurol. Neurosurg.* 92(4):305–310. These highly insoluble aggregates are composed of nonbranching, fibrillar proteins with the common characteristic of a β-pleated sheet conformation. In the CNS, amyloid can be present in cerebral and meningeal blood vessels (cerebrovascular deposits) and in brain parenchyma (plaques). Neuropathological studies in human and animal models indicate that cells proximal to amyloid deposits are disturbed in their normal functions (Mandybur (1989) *Acta Neuropathol.* 78:329–331; Kawai et al. (1993) *Brain Res.* 623:142–6; Martin et al. (1994) *Am. J. Pathol.* 145:1348–1381; Kalaria et al. (1995) *Neuroreport* 6:477–80; Masliah et al. (1996) *J. Neurosci.* 16:5795–5811). AD studies additionally indicate that amyloid fibrils may actually initiate neurodegeneration (Lendon et al. (1997) *J. Am. Med. Assoc.* 277:825–31; Yankner (1996) *Nat. Med.* 2:850–2; Selkoe (1996) *J. Biol. Chem.* 271:18295–8; Hardy (1997) *Trends Neurosci.* 20:154–9).

AD and CAA share biochemical and neuropathological markers, but differ somewhat in the extent and location of amyloid deposits as well as in the symptoms exhibited by affected individuals. The neurodegenerative process of AD, the most common cause of progressive intellectual failure in aged humans, is characterized by the progressive and irreversible deafferentation of the limbic system, association neocortex, and basal forebrain accompanied by neuritic plaque and tangle formation (for a review see Terry et al. (1994) "Structural alteration in Alzheimer's disease." In: Alzheimer's disease (Terry et al. eds.), pp. 179–196. Raven Press, New York). Dystrophic neurites, as well as reactive astrocytes and microglia, are embedded in the core of these amyloid-associated neurite plaques. Although, the neuritic population in any given plaque is mixed, the plaques generally are composed of spherical neurites that contain synaptic proteins, APP (type I), and fusiform neurites containing cytoskeletal proteins and paired helical filaments (PHF; type II).

CAA patients display various vascular syndromes, of which the most documented is cerebral parenchymal hemorrhage. Cerebral parenchymal hemorrhage is the result of extensive amyloid deposition within cerebral vessels (Hardy (1997) *Trends Neurosci.* 20:154–9; Haan et al. (1990) *Clin. Neurol. Neurosurg.* 22:305–10; Terry et al., supra; Vinters (1987) *Stroke* 18:211–24; Itoh et al. (1993) *J. Neurological Sci.* 116:135–41; Yamada et al. (1993) *J. Neurol. Neurosurg. Psychiatry* 5:543–7; Greenberg et al. (1993) *Neurology* 43:2073–9; Levy et al. (1990) *Science* 2:1124–6). In some familial CAA cases, dementia was noted before the onset of hemorrhages (27), suggesting the possibility that cerebrovascular amyloid deposits may also interfere with cognitive functions.

In both AD and CAA, the main amyloid component is the amyloid β protein (Aβ). The Aβ peptide, which is generated from the amyloid β precursor protein (APP) by two putative secretases, is present at low levels in the normal CNS and blood. Two major variants, $A\beta_{1-40}$ and $A\beta_{1-42}$, are produced by alternative carboxy-terminal truncation of APP (Selkoe et al.(1988) *Proc. Natl. Acad. Sci. USA* 85:7341–7345; Selkoe, (1993) *Trends Neurosci* 16:403–409). $A\beta_{1-42}$ is the more fibrillogenic and more abundant of the two peptides in amyloid deposits of both AD and CAA. In addition to the amyloid deposits in AD cases described above, most AD cases are also associated with amyloid deposition in the vascular walls (Hardy (1997), supra; Haan et al. (1990), supra; Terry et al., supra; Vinters (1987), supra; Itoh et al. (1993), supra; Yamada et al. (1993), supra; Greenberg et al. (1993), supra; Levy et al. (1990), supra). These vascular lesions are the hallmark of CAA, which can exist in the absence of AD.

The precise mechanisms by which neuritic plaques are formed and the relationship of plaque formation to the AD-associated, and CAA-associated neurodegenerative processes are not well-defined. However, evidence indicates that disregulated expression and/or processing of APP gene products or derivatives of these gene products derivatives are involved in the pathophysiological process leading to neurodegeneration and plaque formation. For example, missense mutations in APP are tightly linked to autosomal dominant forms of AD (Hardy (1994) *Clin. Geriatr. Med.* 10:239–247; Mann et al. (1992) *Neurodegeneration* 1:201–215). The role of APP in neurodegenerative disease is further implicated by the observation that persons with Down's syndrome who carry an additional copy of the human APP (hAPP) gene on their third chromosome 21 show an overexpression of hAPP (Goodison et al. (1993) *J. Neuropathol. Exp. Neurol.* 52:192–198; Oyama et al. (1994) *J. Neurochem.* 62:1062–1066) as well as a prominent tendency to develop AD-type pathology early in life (Wisniewski et al. (1985) *Ann. Neurol.* 17:278–282). Mutations in Aβ are linked to CAA associated with hereditary cerebral hemorrhage with amyloidosis (Dutch (HCHWA-D) (Levy et al. (1990), supra), in which amyloid deposits preferentially occur in the cerebrovascular wall with some occurrence of diffuse plaques (Maat-Schieman et al. (1994) *Acta Neuropathol.* 88:371–8; Wattendorff et al. (1995) *J. Neurol. Neurosurg. Psychiatry* 5:699–705). A number hAPP point mutations that are tightly associated with the development of familial AD encode amino acid changes close to either side of the Aβ peptide (for a review, see, e.g., Lannfelt et al. (1994) *Biochem. Soc Trans.* 22:176–179; Clark et al. (1993) *Arch. Neurol.* 50:1164–1172). Finally, in vitro studies indicate that aggregated Aβ can induce neurodegeneration (see, e.g., Pike et al. (1995) *J. Neurochem.* 64:253–265).

APP is encoded by a 19-exon gene: exons 1–13, exon 13a, and 14–18 (Yoshikai et al. (1990) *Gene* 82:257–263; see FIG. 1 for a map of the hAPP exon-intron organization of the hAPP gene). Alternative splicing of APP gene-derived transcripts results in at least 10 isoforms (Sandbrink et al. (1994) *J. Biol. Chem.* 269:1510–1517). The predominant transcripts are APP695 (exons 1–6, 9–18, not 13a), APP751 (exons 1–7, 9–18, not 13a) and APP770 (exons 1–18, not 13a). All of these encode multidomain proteins with a single membrane-spanning region. They differ in that APP751 and APP770 contain exon 7, which encodes a serine protease inhibitor domain. APP695 is a predominant form in neuronal tissue, whereas APP751 is the predominant variant elsewhere. Aβ amyloid is derived from that part of the protein encoded by parts of exons 16 and 17.

In three APP mutants, valine-642 in the transmembrane domain of APP(695) is replaced by isoleucine, phenylalanine, or glycine in association with dominantly inherited familial Alzheimer disease. (According to an earlier numbering system, val642 was numbered 717 and the 3 mutations were V717I, V717F, and V717G, respectively.) Yamatsuji et al. ((1996) *Science* 272:1349–1352) concluded that these three mutations account for most, if not all, of the chromosome 21-linked Alzheimer disease. Suzuki et al. ((1994) *Science* 264:1336–1340) suggested that these mutations may cause Alzheimer disease by altering β-APP processing in a way that is amyloidogenic. They found that the APP-717 mutations were consistently associated with a 1.5- to 1.9-fold increase in the percentage of longer Aβ fragments generated and that the longer fragments formed insoluble amyloid fibrils more rapidly than did the shorter ones. In transgenic mice, overexpression of such mutants mimics the neuropathology of AD.

Several transgenic animals expressing human APP (hAPP) have been developed as models for AD (Higgins et al. (1994) *Ann. Neurol* 35:598–607; Mucke et al. (1994) *Brain Res.* 666:151–167; Games et al. (1995) *Nature* 373:523–527; Games et al. (1995) *Soc. Neurosci Abstr.* 21:258). Most transgenic models were designed based on the observation that a number of APP mutations cosegregate with the familial form of AD; patients carrying these APP mutations exhibit neuropathological alterations that are indistinguishable from sporadic AD (Chartier-Harlin et al. (1991) *Nature* 353:844–846; Goate et al. (1991) *Nature* 349:704; Murrell et al. (1991) *Science* 254:97–99; Clark et al. (1993) *Arch. Neurol.* 50:1164–1172). Moreover, APP717 mutations result in an overproduction of the highly amyloidogenic $A\beta_{1-42}$ relative to other Aβ peptides (Suzuki et al. (1994) *Science* 264:1336–1340).

At least one of these transgenic animal models exhibits AD-like neuropathology (Games et al. (1995) *Nature* 373:523–527; Masliah et al. (1996) *J. Neurosci.* 16:5795–5811). The transgenic mouse of Games et al. carries an hAPP minigene (PDAPP), where expression of the PDAPP minigene is driven by a platelet-derived growth factor-B chain (PDGF-B) promoter (Games et al (1995) *Nature* 373:523–527; Rockenstein et al. (1995) *J. Biol. Chem.* 270:28257–28267). The hAPP minigene encodes an alternatively spliced hAPP containing the mutation V→F (valine to phenylalanine) at residue 717 ($APP_{717V \rightarrow F}$), a mutation associated with familial AD (Chartier-Harlin et al. (1991), supra; Murrell et al. (1991), supra; Clark et al. (1993), supra). The PDAPP minigene contains three modified hAPP introns that differed from the corresponding authentic hAPP gene introns by large deletions (introns 6 and 8) or insertion of four nucleotides (intron 7) (Rockenstein et al. (1995), supra). The PDAPP transgenics exhibited four to six-fold higher levels of total APP mRNA relative to nontransgenic animals. In addition, the transgenics' endogenous APP mRNA levels were reduced, resulting in a high ratio of mRNA encoding mutated hAPP versus wild-type murine APP.

The PDAPP transgenic animal of Games et al. ((1995), supra) exhibited both age- and brain region-dependent development of typical amyloid plaques, dystrophic neurites, loss of presynaptic terminals, astrocytosis, and microgliosis. The brains showed typical pathologic findings of AD, including numerous extracellular thioflavin S-positive A-beta deposits, neuritic plaques, synaptic loss, astrocytosis, and microgliosis. Aβ deposits were observed primarily in the hippocampus and cerebral cortex; moreover, Aβ deposits increased with the animal's age.

Hsiao et al. ((1996) *Science* 274:99–102) produced transgenic mice overexpressing the 695-amino acid isoform of human APP containing a K670N, M671L double mutation, which was described by Mullan et al. ((1992) *Nature Genet.* 1:345–349) in a large Swedish family with early-onset Alzheimer disease. Hsiao et al. ((1996) *Science* 274:99–102) reported that a 5-fold increase in the concentration of the β amyloid derivatives was found in the brains of the older transgenic mice; older mice showed impairment in both learning and memory in spatial reference and alternation tasks. Classic senile plaques with dense amyloid cores were present in mice with elevated brain beta amyloid.

Although presently available transgenic animals are promising model for AD and AD-related neuropathologies, the amount of time required to detect AD-like pathology is quite long. For example, the transgenic mice of Games et al. ((1995), supra) exhibited no obvious pathology between four to six months of age. Although Games et al.'s transgenics began to exhibit deposits of human Aβ at about six to nine months, with many deposits observable by eight months, it was not until the transgenic animals were about nine months old or older that the density of plaques increased so that the Aβ-staining pattern resembled that of AD (Games et al., (1995), supra). Likewise, the transgenic animals of Hsaio et al. had normal learning and memory in spatial reference and alternation tasks at 3 months of age; impairment in these characteristics were not apparent until the transgenics were 9 to 10 months of age.

The development of animal models for AD and CAA is a critical step for both understanding these diseases and developing therapeutic drugs. However, the present AD animal models are less desirable, at least in part, because the transgenic animals must be maintained for nearly a year before AD-like pathology is observable, thus significantly slowing the ability to assess the prophylactic or therapeutic effects of candidate drugs for AD and/or AD-like conditions. Worse still, there are no suitable models to study CAA. Thus, there is a clear need in the field for an animal model of AD and CAA.

SUMMARY OF THE INVENTION

The present invention features non-human transgenic animal models for Alzheimer's disease (AD) and CAA, wherein the transgenic animal is characterized by 1) overexpression of bioactive transforming growth factor-β1 (TGF-β1) or 2) both overexpression of bioactive TGF-β1 and expression of a human amyloid β precursor protein (APP) gene product. The transgenic animals may be either homozygous or heterozygous for these alterations. Bigenic animals are further characterized by development of AD-associated and/or CAA-associated pathology within about two to three months of age.

In another aspect the invention features a method of screening for biologically active agents that modulate phenomena associated with AD or CAA (e.g., plaque formation, deposition of APP, expression of APP, etc.), wherein the method involves the steps of combining a candidate agent with a non-human animal transgenic for either 1) bioactive TGF-β1 or 2) bioactive TGF-β1 and an amyloid precursor protein (APP) (preferably a human APP (hAPP)) gene product, and determining the effect of said agent upon a phenomenon associated with AD and/or CAA.

A primary object of the invention is to provide a transgenic animal model for examining the effects of a candidate agent (e.g., a small molecule drug or an endogenous factor) on a phenomenon associated with AD or CAA. Such transgenic animal models are useful for screening candidate agents for use in treating or relieving the symptoms of AD and/or CAA.

Another object is to provide an animal model for AD and CAA pathologies, thereby providing a means to study these conditions.

An advantage of the claimed invention is that the transgenic animal models described and claimed herein exhibit phenomena associated with AD and/or CAA pathologies (e.g., deposition of APP, plaque formation, etc.). Moreover, the transgenic animal models of the invention develop AD-associated pathology more quickly than do conventional transgenic AD animal models.

These and other objects, advantages and features of the present invention will become apparent to those persons skilled in the art upon reading the details of the invention more fully set forth below.

DETAILED DESCRIPTION OF THE INVENTION

Figure 1:
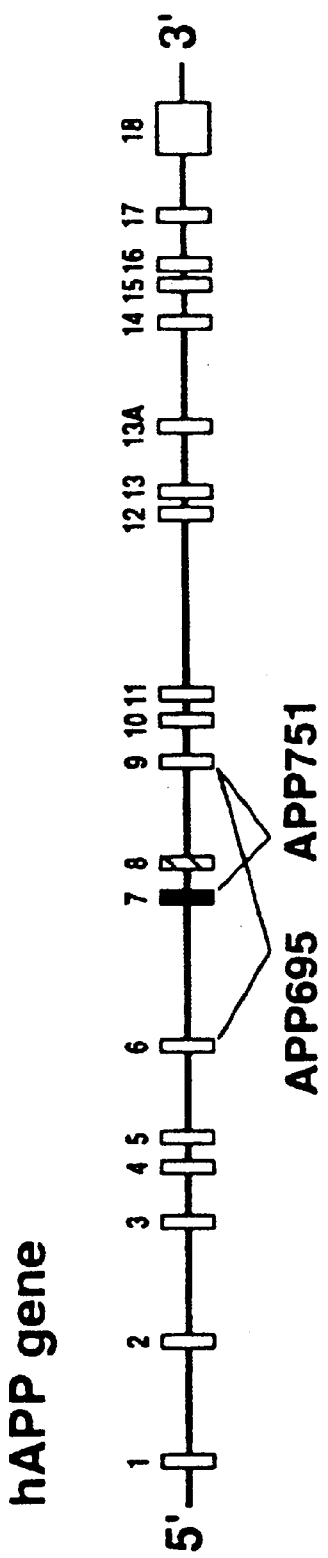
FIG. 1 is a map of the exon-intron organization of the hAPP gene. Boxes represent exons, closed and hatched boxes represent isoform-specific exons as shown. Horizontal lines indicate introns. The entire gene is approximately 400 kb in length.

Before the present transgenic animals and uses therefor are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise.

Thus, for example, reference to "a construct" includes a plurality of such constructs and reference to "the TGF-β1-encoding nucleic acid" and "the hAPP-encoding nucleic acid" includes reference to one or more TGF-β1-encoding nucleic acids and to one or more hAPP-encoding nucleic acids, respectively, and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

DEFINITIONS

The term "transgene" is used herein to describe genetic material which has been or is about to be artificially inserted into the genome of a mammal, particularly a mammalian cell of a living animal.

By "Alzheimer's disease" (abbreviated herein as "AD") is meant a condition associated with formation of neuritic plaques comprising amyloid β protein primarily in the hippocampus and cerebral cortex, as well as impairment in both learning and memory. "AD" as used herein is meant to encompass both AD as well as AD-type pathologies.

By "AD-type pathology" is meant a combination of CNS alterations including, but not limited to, formation of neuritic plaques containing amyloid β protein in the hippocampus and cerebral cortex. Such AD-type pathologies can include, but are not necessarily limited to, disorders associated with aberrant expression and/or deposition of APP, overexpression of APP, expression of aberrant APP gene products, and other phenomena associated with AD. Exemplary AD-type pathologies include, but are not necessarily limited to, AD-type pathologies associated with Down's syndrome that is associated with overexpression of APP.

By "phenomenon associated with Alzheimer's disease" is meant a structural, molecular, or functional event. associated with AD, particularly such an event that is readily assessable in an animal model. Such events include, but are not limited to, amyloid deposition, neuropathological developments, learning and memory deficits, and other AD-associated characteristics.

By "cerebral amyloid angiopathy" (abbreviated herein as CAA) is meant condition associated with formation of amyloid deposition within cerebral vessels which can be complicated by cerebral parenchymal hemorrhage. CAA is also associated with increased risk of stroke as well as development of cerebellar and subarachnoid hemorrhages (Vinters (1987) *Stroke* 18:311–324; Haan et al. (1994) *Dementia* 5:210–213; Itoh et al. (1993) *J. Neurol. Sci.* 116:135–414). CAA can also be associated with dementia prior to onset of hemorrhages. The vascular amyloid deposits associated with CAA can exist in the absence of AD, but are more frequently associated with AD.

By "phenomenon associated with cerebral amyloid angiopathy" or is meant a molecular, structural, or functional event associated with CAA, particularly such an event that is readily assessable in an animal model. Such events include, but are not limited to, amyloid deposition, cerebral parenchymal hemorrhage, and other CAA-associated characteristics.

By "β amyloid deposit" is meant a deposit in the brain composed of Aβ as well as other substances.

By "transformation" is meant a permanent or transient genetic change, preferably a permanent genetic change, induced in a cell following incorporation of new DNA (i.e., DNA exogenous to the cell). Where the cell is a mammalian cell, a permanent genetic change is generally achieved by introduction of the DNA into the genome of the cell.

By "transgenic animal" is meant a non-human animal, usually a mammal (e.g., mouse, rat, rabbit, hamster, etc.), having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

By "bigenic" animal is meant a transgenic animal having at least two transgenes, preferably a first transgene encoding bioactive TGF-β1 and a second transgene encoding a human APP.

A "knock-out" of a gene means an alteration in the sequence of the gene that results in a decrease of function of the target gene, preferably such that target gene expression is undetectable or insignificant. A knock-out of an endogenous APP gene means that function of the APP gene has been substantially decreased so that expression is not detectable or only present at insignificant levels. "Knock-out" transgenics can be transgenic animals having a heterozygous knock-out of the APP gene or a homozygous knock-out of the APP gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic)) of the target gene, e.g., by introduction of an additional copy of the target gene, or by operatively inserting a regulatory sequence that provides for enhanced expression of an endogenous copy of the target gene. "Knock-in" transgenics of interest for the present invention can be transgenic animals having a knock-in of the animal's endogenous APP, the animals' endogenous TGF-β1, or both. Such transgenics can be heterozygous knock-in for the APP gene, homozygous for the knock-in of the APP gene, heterozygous for the knock-in of the TGF-β1 gene, homozygous for the knock-in of the TGF-β1 gene, or any combination of APP homozygous/heterozygous and TGF-β1 homozygous/heterozygous. "Knock-ins" also encompass conditional knock-ins.

By "construct" is meant a recombinant nucleic acid, generally recombinant DNA, that has been generated for the purpose of the expression of a specific nucleotide sequence (s), or is to be used in the construction of other recombinant nucleotide sequences.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by an APP sequence).

OVERVIEW OF THE INVENTION

The invention provides non-human transgenic animal models useful for screening agents useful in the modulation of Alzheimer's disease (AD) and/or cerebral amyloid angiopathy (CAA). The animals are genetically altered so as to either 1) overexpress bioactive transforming growth factor β-1 (TGF-β1) or 2) overexpress bioactive TGF-β-1 and express (or overexpress) an amyloid precursor protein (APP; preferably a human APP (hAPP)). The transgenic animals may be either homozygous or heterozygous for the genetic alteration. The subject animals are useful for testing candidate agents for treatment of individuals diagnosed with AD or CAA, either prophylactically or after disease onset.

The invention is based on the discovery that overexpression of bioactive TGF-β1 in transgenic mice induces the accumulation of Aβ immunoreactive amyloid deposits in cerebral blood vessels and meninges, thus providing an animal model for CAA. The invention is also based on the discovery that co-expression of TGF-β1 in hAPP transgenic mice resulted in cerebrovascular deposition of human Aβ at 2–3 months of age. The bigenic mice develop prominent vascular amyloid deposits, which have not been demonstrated in singly hAPP singly transgenic mice. This discovery thus provides an animal model for CAA, which is associated with such vascular amyloid deposits. Moreover, bigenic mice reveal amyloid deposits earlier than singly transgenic APP mice, which do not normally develop AD-type pathology until 6–8 months of age. This latter discovery provides for transgenic AD animal models that develop molecular and structural manifestations of AD at a stage much earlier than in other transgenic AD animal models.

Singly transgenic animals overexpressing bioactive TGF-β1 and bigenic animals overexpressing bioactive TGF-β1 and expressing (or overexpressing) APP are both useful as models for either AD or CAA. Bigenic mice may be preferably as an animal model for AD in that amyloid deposits occur early in the life of the animal and are combined with parenchymal and vascular deposits associated with AD.

Transgenic Animals

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc. Preferably, the transgenic-animals are mice.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The exogenous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

In general, the transgenic animals of the invention comprise genetic alterations to provide for 1) expression of bioactive TGF-β1, or 2) expression of bioactive TGF-β1 and expression of a desired APP sequence (e.g., human APP). Preferably the introduced sequences provide for high expression of APP and low to high expression of TGF-β1. Specific APP- and TGF-β1-encoding constructs of interest are described below. Of particular interest and importance is the expression of a bioactive form of TGF-β1, preferably a TGF-β1 having serines substituted for the cysteines at positions 223 and 225 of the TGF-β1 pro-peptide (see Samuel et al. (1992) *EMBO J.* 11:1599–1605; Brunner (1989) *J. Biol. Chem.* 264:13660).

The transgenic animals of the invention can comprise other genetic alterations in addition to the presence of the TGF-β1-encoding sequence or the TGF-β1 and APP-encoding sequences. For example, the host's genome may be altered to affect the function of endogenous genes (e.g., endogenous APP and/or TGF-β1 genes), contain marker genes, or other genetic alterations consistent with the goals of the present invention.

Knockouts and Knockins

Although not necessary to the operability of the invention, the transgenic animals described herein may comprise alterations to endogenous genes in addition to (or alternatively for TGF-β1), to the genetic alterations described above. For example, the host animals may be either "knockouts" and/or "knockins" for a target gene(s) as is consistent with the goals of the invention (e.g., the host animal's endogenous APP may be "knocked out" and/or the endogenous TGF-β1 gene "knocked in"). Knockouts have a partial or complete loss of function in one or both alleles of an endogenous gene of interest (e.g., APP). Knockins have an introduced transgene with altered genetic sequence and/or function from the endogenous gene. The two may be combined, for example, such that the naturally occurring gene is disabled, and an altered form introduced. For example, it may be desirable to knockout the host animal's endogenous APP gene, while introducing an exogenous APP gene (e.g., a human APP gene).

In a knockout, preferably the target gene expression is undetectable or insignificant. For example, a knock-out of an APP gene means that function of the APP has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the "knock-out". A chromosomal deletion of all or part of the native gene may be induced, including deletions of the non-coding regions, particularly the promoter region, 3' regulatory sequences, enhancers, or deletions of gene that activate expression of APP genes. A functional knock-out may also be achieved by the introduction of an anti-sense construct that blocks expression of the native genes (for example, see Li and Cohen (1996) *Cell* 85:319–329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

It should be noted that while a TGF-β1 and/or host APP gene can be knocked out in the transgenic animals of the invention, it is not necessary to the utility of either the singly transgenic TGF-β1 animal or the bigenic TGF-β1/hAPP animal.

A "knockin" of a target gene means an alteration in a host cell genome that results in altered expression or function of a native target gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or represser. The use of knockin technology may be combined with production of exogenous sequences to produce the transgenic animals of the invention. For example, the APP/TGF-β1 transgenic animals of the invention may contain a knockin of the host's endogenous TGF-β1-encoding sequences to provide for the desired level of TGF-β1 expression, and contain an exogenous APP-encoding sequence.

Where the transgenic animal is a bigenic TGF-β1/APP animal, the APP animal, which can be, for example, subsequently crossed with a TGF-β1 singly transgenic animal, can be produced using the methods and compositions described in U.S. Pat. No. 5,604,131 (describing non-human animals transgenic for production of APP695, APP751, and/or APP770); U.S. Pat. No. 5,612,486 (describing production of non-human animals transgenic for an APP polypeptide comprising the Swedish mutation); and WO 9640895, published Dec. 19, 1996 (describing animals transgenic for amino acids 672–714 of human APP; each of which is hereby incorporated by reference for such disclosures relating to compositions and methods useful in the production of APP-expressing animals useful in the present invention.).

Nucleic Acid Compositions

Constructs for use in the present invention include any construct suitable for use in the generation of transgenic animals having the desired levels of expression of a desired APP-encoding sequence and/or of bioactive TGF-β1. Methods for isolating and cloning a desired sequence, as well as suitable constructs for expression of a selected sequence in a host animal, are well known in the art. The construct can include sequences other than the APP and/or TGF-β1-encoding sequences. For example, a detectable marker, such as lac Z may be included in the construct, where upregulation of expression of the encoded sequence will result in an easily detected change in phenotype.

The APP-encoding construct can contain a wild-type sequence encoding APP (providing the APP sequence when expressed in conjunction with TGF-β1 in the host animal, results in AD-like pathology) or mutant forms of APP, especially those associated with AD in humans. Likewise, the TGF-β1-encoding construct can contain a wild-type TGF-β1-encoding sequence or a sequence encoding a modified TGF-β1, particularly where the modification provides for a desired level of TGF-β1 expression. Regardless of the precise construct used, the encoded TGF-β1 should be a bioactive form of TGF-β1.

The terms "APP gene" and "TGF-β1 gene" are used generically to mean APP genes and TGF-β1 genes, e.g. homologs from rat, human, mouse, guinea pig, etc., and their alternate forms. "APP gene" as used herein is meant to particularly encompass isoforms and mutants thereof associated with AD and/or AD-type pathologies. "APP gene" and "TGF-β1 gene" are also intended to mean the open reading frame encoding specific polypeptides, introns, and adjacent 5' and 3' non-coding nucleotide sequences involved in the regulation of expression, up to about 1 kb beyond the coding region, but possibly further in either direction. The DNA sequences encoding APP and/or TGF-β1 may be cDNA or genomic DNA or a fragment thereof. The genes may be introduced into an appropriate vector for extrachromosomal maintenance or for integration into the host.

The genomic sequences of particular interest comprise the nucleic acid present between the initiation codon and the stop codon, including all of the introns that are normally present in a native chromosome. They may further include the 3' and 5' untranslated regions found in the mature mRNA. They may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kb or smaller; and substantially free of flanking chromosomal sequence.

The sequences of the 5' regions of the APP gene, and further 5' upstream sequences and 3' downstream sequences, may be utilized for promoter elements, including enhancer binding sites, that provide for expression in tissues where APP is normally expressed. The tissue specific expression is useful for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1:194–205; Mortlock et al. (1996) *Genome Res.* 6:327–33; and Joulin and Richard-Foy (1995) *Eur J Biochem* 232:620–626.

The nucleic acid compositions used in the subject invention may encode all or a part of APP and TGF-β1 as appropriate. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used.

Several isoforms and homologs of both APP and TGF-β1 have been isolated and cloned. Additional homologs of cloned APP and/or TGF-β1 are identified by various methods known in the art. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity may be determined by hybridization under stringent conditions, for example, at 50° C. or higher and 0.1×SSC (9 mM saline/0.9 mM sodium citrate). By using probes, particularly labeled probes of DNA sequences, one can isolate homologous or related genes. The source of homologous genes may be any species, e.g. primate, rodents, canines, felines, bovines, ovines, equines, etc.

Where desirable, the APP and/or TGF-β1 sequences, including flanking promoter regions and coding regions, may be mutated in various ways known in the art to generate targeted changes in the sequence of the encoded protein, splice variant production, etc. The sequence changes may be substitutions, insertions or deletions. Deletions may include large changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of APP and/or TGF-β1, or to alter properties of the proteins that affect their function or regulation.

Techniques for in vitro mutagenesis of cloned genes are known. Examples of protocols for scanning mutations may be found in Gustin et al., 1993 Biotechniques 14:22 ; Barany, 1985 Gene 37:111–23; Colicelli et al., 1985 Mol Gen Genet 199:537–9; and Prentid et al., 1984 Gene 29:303–13. Methods for site specific mutagenesis can be found in Sambrook et al., 1989 Molecular Cloning: A Laboratory Manual, CSH Press, pp. 15.3–15.108; Weiner et al., 1993 Gene 126:35–41; Sayers et al., 1992 Biotechniques 13:592–6; Jones and Winistorfer, 1992 Biotechniques 12:528–30; Barton et al., 1990 Nucleic Acids Res 18:7349–55; Marotti and Tomich, 1989 Gene Anal Tech 6:67–70; and Zhu 1989 Anal Biochem 177:120–4.

The APP gene, the TGF-β1 gene, and exemplary derivatives thereof suitable for use in the production of the transgenic animals of the invention are described below.

The TGF-β1 Gene

The TGF-β1-encoding sequence introduced into the bigenic animals of the invention can be any bioactive form of TGF-β1. Preferably, the TGF-β1 transgene is overexpressed in the host animal (e.g., the transgene provides for increased levels of TGF-β1 production relative to wild-type, e.g., more particularly a level of TGF-β1 expression to facilitate early onset of AD when co-expressed with an APP gene). The TGF-β1-encoding sequence can be either genomic or cDNA, preferably cDNA, and can be derived from any source, e.g., human, murine, porcine, bovine, etc. Several TGF-β1 sequences have been isolated, cloned, and sequenced. Table 1 provides a list of TGF-β1 sequences that may be suitable for use in the present invention, as well as Genbank accession numbers relating to such sequences.

TABLE 1

| TGF-β1 Sequence | Reference or GenBank Accession No. | TGF-β1 Sequence | Reference or GenBank Accession No. |
| --- | --- | --- | --- |
| Human TGF-β1 precursor | AA459172 | Bovine TGF-β1 | M36271 |
| Human TGF-β1 | E00973; X02812; J05114; M38449; M55656 | Sheep (Ovis) TGF-β1 | X76916; L36038 |
| Porcine TGF-β1 | M23703; X12373 | Canine TGF-β1 | L34956 |
| Hamster TGF-β1 | X60296 | Rat TGF-β1 | X52498 |
| Murine TGF-β1 | M13177 | | |

The transgene encoding TGF-β1 should preferably provide for expression and secretion of the polypeptide as a bioactive peptide. Expression of TGF-β1 in the host animal can be either constitutive or inducible. TGF-β1 expression may be either systemic or tissue-specific, preferably tissue-specific (e.g., expression of TGF-β1 substantially specifically in astrocytes). Expression of the TGF-β1-encoding sequence is driven by a promoter, preferably by the glial fibrillary acidic protein (GFAP) gene promoter.

Preferably, the TGF-β1 transgenic animals overproduce bioactive TGF-β1 relative to control, non-transgenic animals. For example, TGF-β1 transgenic animals preferably exhibit TGF-β1 mRNA levels in brain tissue that are greater than TGF-β1 mRNA levels in brain tissue of non-transgenic animals. Preferably, the TGF-β1 mRNA levels in brain tissue are elevated by about one- to two-fold in heterozygous TGF-β1 animals, and about five-to six-fold in homozygous TGF-β1 animals, relative to TGF-β1 mRNA levels in non-transgenic control animals (e.g., in littermate control animals). Furthermore, the TGF-β1 transgenic animals preferably overproduce TGF-β1 from astrocytes at levels least about three to five times higher than from normal non-transgenic astrocytes. Methods for assessment of TGF-β1 mRNA levels and assessment of TGF-β1 production levels from astrocytes, as well as other methods for assessing TGF-β1 production and activity are well known in the art (see, e.g,. Wyss-Cory et al. (1995) *Am. J. Pathology* 147:53–67).

The TGF-β1 encoding sequence may also be provided as a fusion protein. Methods for production of TGF-β1 constructs are well known in the art (see, e.g., Wyss-Coray et al. (1995) *Am. J. Pathol.* 147:53–67).

The APP Gene and its Derivatives Suitable for Use in the Present Invention

The APP gene contains 19 exons. Three of these exons (exons 7, 8, and 15) are subject to alternative splicing. The different APP isoforms derived from the APP gene are designated according to the number of amino acids. The longest isoform identified to date, APP770, contains a first domain of 56 amino acids (encoded by exon 7) and a second adjacent 19 amino acid domain (encoded by exon 8). The first domain shares sequence homology with, and can function like, Kunitz-type serine protease inhibitors (KPI), while the second domain shares homology with the MRC-OX-2 antigen, which is found on the surface of neurons and certain immune cells (Mucke et al. (1994) *Brain Res.* 666:1510167; Jacobsen et al. (1991) *Neurobiol. Aging* 12:585–592; Golde et al. (1990) *Neuron* 4:2530267). APP695 lacks both of the domain so APP770, and is produced primarily by neurons, which are the primary source of APP within the central nervous system (Neve et al. (1988) Neuron 1:669–677; Tanzi et al. (1993) *Brain Res. Mol. Brain Res.* 18:246–252). APP 751 contains the KPI domain (exon 7) but lack the OX-2 domain (exon 8). Cultured astrocytes and microglia express predominantly KIP-encoding APP mRNAs. Brain tissue expresses little APP770 and low intermediate, or high level of APP751, depending upon the animal species and brain region analyzed. For a comprehensive quantitation of different APP splice products in the central nervous system, see Sandbrink et al. (1994) *J. Biol. Chem.* 262:1510–1517.

Transgenic animals of the present invention comprise a heterologous sequence encoding a desired APP gene, preferably a human APP gene. Preferably, the host animal produces high levels of $A\beta_{1-42}$, more preferably human $A\beta_{1-42}$, in the brain. Preferably, the APP gene is encodes a genomic APP sequence or a sequence encoding a spliced APP gene (e.g., a cDNA), more preferably an APP cDNA sequence. Where the transgene is an APP cDNA, the APP gene can be any APP gene splice variant, preferably a splice variant associated with AD and/or an AD-type pathology. For example, the transgene can encode APP695 (exons 1–6, 9–18, not 13a), APP751 (exons 1–7, 9–18, not 13a) or APP770 (exons 1–18, not 13a), preferably APP695 and/or APP 751. Alternatively, the APP gene can be an mutant, particularly an APP mutant associated with AD and/or an AD-type pathology. Mutants of particular interest include mutants comprising a substitution at valine-642 in the transmembrane domain of APP(695) with isoleucine, phenylalanine, or glycine (also referred to in the art as V717I, V717F, and V717G, respectively).

Preferably, the transgene comprises a human APP (hAPP) gene which is capable of undergoing alternative splicing in the host animal to produce the splice variants hAPP770, hAPP751, and hAPP695. More preferably, the transgenic animal produces high levels of human $A\beta_{1-42}$ in the brain. Alternatively, the animals may be made transgenic for a sequence encoding the Aβ polypeptide (amino acid residues 1–42 of APP) rather than for the full-length APP-encoding sequence.

The host animals can be homozygous or heterozygous for the APP-encoding sequence, preferably homozygous. The APP gene can also be operably linked to a promoter to provide for a desired level of expression in the host animal and/or for tissue-specific expression. Expression of APP can be either constitute or inducible, preferably constitutive. Preferably, APP gene expression is driven by a strong promoter, preferably a PDGF promoter.

APP genes suitable for use in the present invention have been isolated and sequenced. Table 2 provides a list of human APP sequences useful in the production of the transgenes of the present invention, and provides Genbank accession numbers relating to the listed APP sequences.

TABLE 2

Human APP Sequences

| APP Sequence | Reference or GenBank Accession No. | APP Sequence | Reference or GenBank Accession No. |
|---|---|---|---|
| hAPP exon 1 | M34862 | hAPP exon 11 | M34872 |
| hAPP exon 2 | M34863 | hAPP exon 12 | M34873 |
| hAPP exon 3 | M34864 | hAPP exon 13 | M34874 |
| hAPP exon 4 | M34865 | hAPP exon 13a | M34875 |
| hAPP exon 5 | M34866 | hAPP exon 14 | M34876 |
| hAPP exon 6 | M34867 | hAPP exon 15 | M34877 |
| hAPP exon 7 | M34868 | hAPP exon 16 | M34878 |
| hAPP exon 8 | M34869 | hAPP exon 17 | M34879 |
| hAPP exon 9 | M34870 | hAPP exon 18 | M33112 |
| hAPP exon 10 | M34871 | human Aβ cDNA | M16765; Y00264 |

Methods of Making Transgenic Animals

DNA constructs for random integration need not include regions of homology to mediate recombination. Where homologous recombination is desired, the DNA constructs will comprise at least a portion of the target gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

Where bigenic TGF-β1/APP animals are desired, the mice are preferably generated by crossing a singly transgenic TGF-β1 animal with a singly transgenic APP animal and identifying bigenic animals according to methods well known in the art.

Drug Screening Assays

Through use of the subject transgenic animals or cells derived therefrom, one can identify ligands or substrates that modulate phenomena associated with AD, e.g., amyloid deposition, neurodegeneration, and/or behavioral phenomena, and/or with CAA, e.g., amyloid deposition on cerebrovascular walls, cerebral hemorrhage, etc. Of particular interest are screening assays for agents that have a low toxicity for human cells.

A wide variety of assays may be used for this purpose, including behavioral studies, determination of the localization of drugs after administration, immunoassays to detect amyloid deposition, and the like. Depending on the particular assay, whole animals may be used, or cells derived therefrom. Cells may be freshly isolated from an animal, or may be immortalized in culture. Cells of particular interest are derived from neural tissue.

The term "agent" as used herein describes any molecule, e.g. protein or pharmaceutical, with the capability of affecting the molecular and clinical phenomena associated with AD and/or CAA. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Antibodies specific for and APP gene product polypeptide may be used in screening immunoassays, particularly to detect amyloid proteins (AP) in neurite plaques, or to qualitatively or quantitatively determine the amount of AP in a cell or sample. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

A number of assays are known in the art for determining the effect of a drug on animal behavior and other phenomena associated with AD and/or CAA. Some examples are provided, although it will be understood by one of skill in the art that many other assays may also be used. The subject animals may be used by themselves, or in combination with control animals. Control animals may have, for example, a wild-type APP transgene that is not associated with AD or CAA, or may be transgenic for a control construct that does not contain an APP-encoding and/or TGF-β1-encoding sequence.

The screen using the transgenic animals of the invention can employ any phenomena associated with AD and/or CAA that can be readily assessed in an animal model. The screening for AD can include assessment of phenomena including, but not limited to: 1) analysis of molecular markers (e.g., levels of expression of APP gene products in brain tissue; presence/absence in brain tissue of various APP splice variants, isoforms, and mutants associated with AD; and formation of neurite plaques); 2) assessment behavioral symptoms associated with memory and learning; 3) detection of neurodegeneration characterized by progressive and irreversible deafferentation of the limbic system, association neocortex, and basal forebrain (neurodegeneration can be measured by, for example, detection of synaptophysin expression in brain tissue) (see, e.g., Games et al. (1995) Nature 373:523–7). The screening for CAA can include assessment of phenomena including, but not limited to: 1) analysis of molecular markers (e.g., levels of expression of APP gene products in brain vascular tissue; presence/absence in brain tissue of various APP splice variants, isoforms, and mutants associated with CAA; formation of cerebrovascular amyloid deposits); and 2) detection of cerebral hemorrhage associated with amyloid deposition. These phenomena may be assessed in the screening assays either singly or in any combination.

Preferably, the screen will include control values (e.g., the level of amyloid production in the test animal in the absence of test compound(s)). Test substances which are considered positive, i.e., likely to be beneficial in the treatment of AD or CAA, will be those which have a substantial effect upon an AD- or CAA-associated phenomenon (e.g., test agents that are able to reduce the level of Aβ production, preferably by at least 20% more preferably by at least 50%, and most preferably by at least 80%).

Methods for assessing these phenomena, and the effects expected of a candidate agent for treatment of AD and/or CAA, are well known in the art. For example, methods for using transgenic animals in various screening assays for, for example, testing compounds for an effect on AD, are found in WO 9640896, published Dec. 19, 1996; WO 9640895, published Dec. 19, 1996; WO 9511994, published May 4, 1995 (describing methods and compositions for in vivo monitoring of Aβ; each of which is incorporated herein by reference with respect to disclosure of methods and compositions for such screening assays and techniques). Examples of assessment of these phenomena are provided below, but are not meant to be limiting.

Pathological Studies

After exposure to the candidate agent, the animals are sacrificed and analyzed by immunohistology for either: 1) neuritic plaques and neurofibrillary tangles (NFTs) in the brain (AD model) and/or 2) amyloid deposition on cerebrovascular walls (CAA). The brain tissue is fixed (e.g, in 4% paraformladehyde) and sectioned; the sections are stained with antibodies reactive with the APP and/or the beta peptide. Secondary antibodies conjugated with fluorescein, rhodamine, horse radish peroxidase, or alkaline phosphatase are used to detect the primary antibody. These experiments permit identification of amyloid plaques and the regionalization of these plaques to specific areas of the brain.

Sections are also stained with other antibodies diagnostic of Alzheimer's plaques, recognizing antigens such as Alz-50, tau, A2B5, neurofilaments, neuron-specific enolase, and others that are characteristic of Alzheimer's and/or CAA plaques. Staining with thioflavins and congo red can also be carried out to analyze co-localization of Aβ deposits within the neuritic plaques and NFTs of AD or along the vascular walls as in CAA.

Analysis of APP and Aβ Expression 1) mRNA: mRNA can be isolated by the acid guanidinium thiocyanatephenol:chloroform extraction method (Chomczynski et al., (1987) Anal Biochem 162:156–159) from cell lines and tissues of transgenic animals to determine expression levels by Northern blots.

2) In situ Hybridizations: Radioactive or enzymatically labeled probes can be used to detect mRNA in situ. The probes are degraded approximately to 100 nucleotides in length for better penetration of cells. The procedure of Chou et al. (1990) J Psychiatr Res 24:27–50 (1990) for fixed and paraffin embedded samples is briefly described below although similar procedures can be employed with samples sectioned as frozen material.

Paraffin slides for in situ hybridization are dewaxed in xylene and rehydrated in a graded series of ethanols and finally rinsed in phosphate buffered saline (PBS). The sections are postfixed in fresh 4% paraformaldehyde. The slides are washed with PBS twice for 5 minutes to remove paraformaldehyde. Then the sections are permeabilized by treatment with a 20 mu g/ml proteinase K solution. The sections are refixed in 4% paraformaldehyde, and basic molecules that could give rise to background probe binding are acetylated in a 0.1M triethanolamine, 0.3M acetic anhydride solution for 10 minutes. The slides are washed in PBS, then dehydrated in a graded series of ethanols and air dried. Sections are hybridized with antisense probe, using sense probe as a control. After appropriate washing, bound radioactive probes are detected by autoradiography or enzymatically labeled probes are detected through reaction with the appropriate chromogenic substrates.

3) Western Blot Analysis: Protein fractions can be isolated from tissue homogenenates and cell lysates and subjected to Western blot analysis as described by Harlow et al., Antibodies: A laboratory manual, (Cold Spring Harbor, N.Y., 1988); Brown et al.,(1983) *J. Neurochem* 40:299–308; and Tate-Ostroff et al., (1989) *Proc Natl Acad Sci* 86:745–749). Only a brief description is given below.

The protein fractions can be denatured in Laemmli sample buffer and electrophoresed on SDS-polyacrylamide gels. The proteins are be then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of APP proteins.

Behavioral Studies of Transgenic Mice and Rats (for AD)

Behavioral tests designed to assess learning and memory deficits can be employed. An example of such as test is the Morris Water maze (Morris (1981) *Learn Motivat* 12:239–260). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues.

Alternatively, or in addition, memory and learning deficits can be studied using a 3 runway panel for working memory impairment (attempts to pass through two incorrect panels of the three panel-gates at four choice points) (Ohno et al. (1997) *Pharmacol Biochem Behav* 57:257–261).

Therapeutic Agents Identified Using the Transgenic Animals of the Invention

The therapeutic agents may be administered in a variety of ways, orally, topically, parenterally e.g. subcutaneously, intraperitoneally, by viral infection, intravascularly, etc. Oral treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Unless indicated otherwise, all transgenic mice were of the Balb/c×SJL background and heterozygous for the respective transgene. Nontransgenic littermates served as controls.

Example 1

Production and Characterization of TGF-β1 Transgenic Animals

Figure 2:
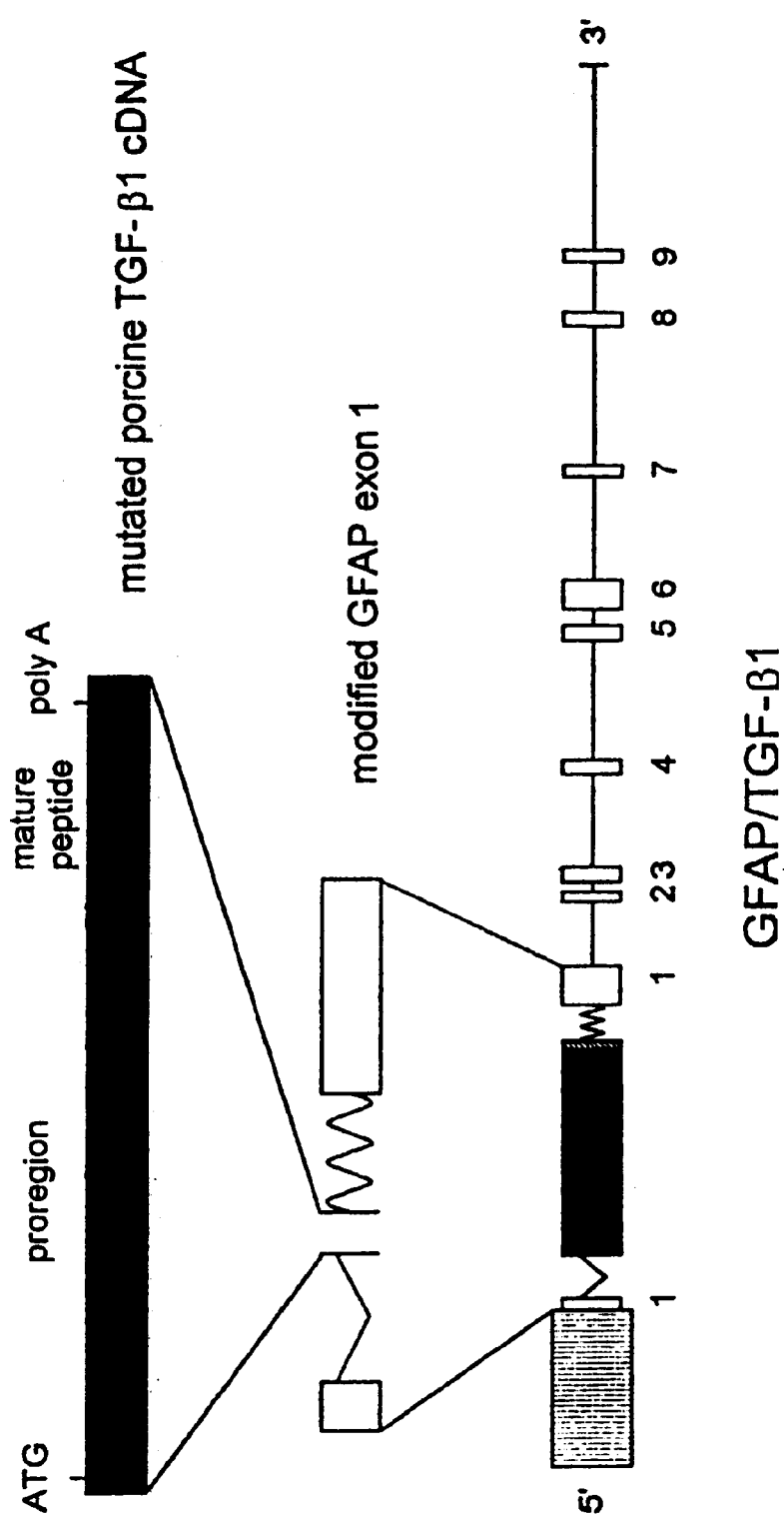
FIG. 2 is a map of the GFAP-TGF-β1 construct used to generate TGF-β1 transgenic animals.

TGF-β1 transgenic mice were produced as described in Wyss-Coray et al. (1995) *Am. J. Pathol.* 147:53–67. Briefly, transgenic mice were from the GFAP-TGF-β1 lines 64 and 115 described previously (Wyss-Coray et al. (1995) supra). Briefly, a 1.35 kb porcine TGF-β1 cDNA was inserted into the first exon of a modified mouse glial fibrillary acidic protein (GFAP) gene (Toggas et al. (1994) *Nature* 367:188–193; Johnson et al. (1995) *Glia* 13:174–184). This cDNA had been mutated to encode serines instead of cysteines at amino acid positions 223 and 225 to ensure that TGF-β1 is secreted as a bioactive peptide. A map of the construct is shown in FIG. 2. The structure of the resulting fusion gene was confirmed by restriction enzyme analysis and sequencing of GFAP/TGF-β1 junctions. The construct was freed from plasmid sequences, purified, and injected into BALB/cxSJL F2, one-cell stage embryos as described by Mucke eta 1. (1991) *New Biol.* 3:465–474. TGF-β1 transgenic mice were identified by slot blot or Southern blot analysis of tail DNA using a 32P-labeled random probe that recognizes the SV40 sequence in the modified GFAP exon 1.

The GFAP-TGF-β1 mice expressed in astrocytes a porcine TGF-β1 cDNA that was mutated to result in the production of bioactive TGF-β1. High-level overexpression of TGF-β1 results in the development of communicating hydrocephalus seizures, incoordination, and runting (Wyss-Coray et al. (1995) supra), low-expresser mice such as those used in the current study develop no such abnormalities (Wyss-Coray et al. (1995), supra).

The mice used in the present examples were the low expresser glial fibrillary acidic protein (GFAP)-TGF-β1 transgenic lines 64 (n=44) and 115 (n=33) (Wyss-Coray et al., supra). Heterozygous mice from line 64 expressed half the levels of cerebral TGF-β1 mRNA than heterozygous mice from line 115.

a) Assessment of TGF-β1 Expression Using Anti-TGF-β1 Antibodies

Brains of the TGF-β1 mice were analyzed for expression of TGF-β1 by immunocytochemistry. As with all tissue processing described herein, the mice and perfusing transcardially with normal saline. Brains were removed and divided sagitally. One hemibrain was snap-frozen; the other was postfixed in freshly prepared 4% paraformaldehyde in 0.1 M phosphate buffer at 40° C. for 48 h. All postfixed brain tissues were stored in 0.1 M phosphate buffer containing 0.1% sodium azide at 4° C. until cutting. Brains were serially sectioned at 40 gm with a VT1000E vibratome (Leica, Nussloch, Germany), and sections were cryoprotected and stored at −20° C. as previously described (Masliah et al. (1992) *Ann. Neurol.* 32:321–329). Vibratome sections of sagittal brain sections from 16-month old TGF-β1 mice and nontransgenic controls were stained with the porcine TGF-β1 specific antiserum G4 using standard immunoperoxidase techniques using ABC kits from Vector Laboratories (Wyss-Cory et al. (1995), supra; Games et al. (1995), supra). Sections were blocked with 10% serum (in phosphate-buffered saline, pH 7.4) from the species in which the secondary antibody was raised. All blocking sera (horse, goat) and secondary antibodies (horse anti-mouse, goat anti-rabbit) were from Vector Laboratories.

Transgene-expression in 16 month old TGF-β1 transgenic mice was found in astrocytes throughout the brain and was most prominent in perivascular locations.

b) Thioflavin S Staining of Brain Sections of TGF-β1 Transgenic Mice

Thioflavin S is an accepted marker of β-pleated amyloid proteins (Vinters (1987) *Stroke* 18:311–324; Terry et al. in *Alzheimer Disease* (eds. Terry et al. ) pgs. 179–196, Raven Press, Ltd. New York, 1994)). Thioflavin S staining was accomplished by air-drying vibratome sections overnight on superfrost slides (Fisher, Pittsburgh, Pa.), fixed to the slides with 4% formaldehyde in 0.1 M phosphate buffer, and stained with a 1% thioflavin S solution for 8 min. Sections were rapidly washed in 100% and twice in 80% of ethanol/water, rinsed for 10 min with water, and mounted with Vecta-shield fluorescence mounting medium (Vector Laboratories, Burlingame, Calif.). Sections were analyzed by laser scanning confocal microscopy with a Bio-Rad MRC-1024 mounted on a Nikon Optiphot-2 microscope as described (Wyss-Coray et al. (1995) *Am. J. Pathol.* 147:53–67; Games et al. (1995) *Nature* 373:523–527; Masliah et al., (1996), supra). The thioflavin S score was determined semiquantitatively by visual inspection of thioflavin S-stained brain sections: Grade 0, no vessels affected, Grade 1, occasional vessels affected, Grades 2–4, multiple vessels affected mildly (Grade 2), moderately (Grade 3), or severely (Grade 4).

Thioflavin S staining showed that by 12 to 18 months of age, heterozygous TGF-β1 mice had many cerebrovascular thioflavin S positive deposits as well as a layer of thioflavin S positive material along the meninges. No such deposits were seen in nontransgenic control mice. Staining in some vessels in TGF-β1 mice showed striking similarities to the staining seen in vessels from AD patients with cerebral amyloid angiopathy. Semiquantitative assessment of cerebral thioflavin S positive deposits in TGF-β1 mice and controls confirmed the strong association between TGF-β1 expression and cerebrovascular amyloid deposition: the mean thioflavin S score was 2.1±0.3 (range 1–4) in TGF-β1 transgenic mice (n=12) but was only 0.1±0.1 (range 0–1) in nontransgenic controls (n=7). In homozygous TGF-β1 mice, clear meningeal and vascular thioflavin S-positive deposits were found as early as one month postnatally (n=6; thioflavin S score, 2.1±0.2; range, 1.5–3), and heterozygous TGF-β1 mice of the higher expresser line showed weak deposits at 8 weeks of age (n=6; thioflavin S score, 0.8±0.1; range, 0–1.5). These Aβ staining patterns in the TGF-β1 singly transgenic mice were similar to the vascular deposits observed in CAA and in most cases of AD.

c) Aβ Antibody Staining

To analyze further the nature of the thioflavin S positive deposits, brain sections from 16- to 18-month-old TGF-β1 mice and nontransgenic controls were labeled with different antibodies raised against Aβ peptides. Specifically, sagittal brain sections prepared as described above were stained with monoclonal antibody 10D5 (against Aβ$_{1-16}$ (10 μg/ml)); 2G3 (mouse anti-Aβ$_{1-42}$ (10 μg/ml); 3D6 (mouseanti-Aβ$_{1-5}$; 3 μg/ml); Rat 1–28 rabbit anti-rat Aβ$_{1-28}$ (1:500; Athena Neurosciences); or R1280 (rabbit anti-human Aβ; Joachim et al. (1989) *Nature* 341:226–230)) (1: 1000).

Antibody immunostaining resulted in distinct labeling of cerebral blood vessels and meninges in aged TGF-β1 mice, but not in age-matched nontransgenic controls with antibodies 10D5, 2G3, Rat 1–28, and R1280, whereas antibody 3D6 did not label the deposits. The lack of staining with 3D6, which is specific for the NH$_2$ terminus of Aβ, could be due to a different length of murine Aβ in these deposits. Semiquantitative scoring of brain sections from 12- to 18-month-old mice immunostained with Aβ antibody 10D5 revealed a highly significant difference between TGF-β1 mice and nontransgenic controls: the mean Aβ score was 1.4±0.4 (range, 0.5–5) in TGF-β1 transgenic (n=12) mice but was only 0.14±0.09 (range, 0–0.5) in non-transgenic controls (n=7).

Comparison of Thioflavin S Staining and Cerebrovascular AD Immunoreactivity in TGF-β1 Transgenic Mice Brain Sections and in Human Brains with AD Thioflavin S staining and immunoreactivity of brain sections from TGF-β1 transgenic mice were compared to thioflavin S staining and immunoreactivity of brain sections of human AD cases. AD cases and controls were from the Alzheimer's Disease Research Center of the University of California at San Diego or from the Sun Health Research Institute in Sun City, Ariz. AD severity was graded clinically using the Blessed score and clinical dementia rating scale and histologically according to the density of thioflavin S stained plaques and tangles in the neocortex and hippocampus, as described previously Terry et al., in *Alzheimer Disease* (eds. Terry et al.) pgs. 179–196 (Raven Press, Ltd. New York, 1994); Rockenstein et al., (1995) supra). Frontal cortex (midfrontal gyrus) from cases with AD (n=15; age 64–88 years) and from non-demented controls (n=7; age 65–77 years) was obtained at autopsy. Tissue blocks were either fixed in formalin or snap-frozen within 8 h after death and stored in 0.1 M phosphate buffer containing 0.1% sodium azide at 4° C. until cutting. Brains were serially sectioned at 40 gm with a VT1000E vibratome, cryoprotected, and stored at –20° C. as described above. The cerebral amyloid angiopathy score was determined semiquantitatively by visual inspection of thioflavin S-stained brain sections: Grade 0, no vessels affected, Grade 1, occasional vessels affected, Grades 2–4, multiple vessels affected mildly (Grade 2), moderately (Grade 3), or severely (Grade 4). Antibody staining was carried out as described above for murine brain sections.

Staining of AD brain sections with thioflavin S or Aβ antibodies revealed that cerebrovascular amyloid deposits in AD cases with mild to moderate cerebral amyloid angiopathy resembled those seen in TGF-β1 mice. Notably, strong, TGF-β1 immunoreactivity was seen around blood vessels in AD cases with severe cerebral amyloid angiopathy, whereas no or only faint TGF-β1 staining was observed in AD cases without cerebral amyloid angiopathy. As reported by others (Van der Wal et al. (1993) *Neuro. Rep.* 4:69–72; Peress et al. (1995) *J. Neuropathol. Exp. Neurol.* 54:802–811), senile plaques and some neurons showed also TGF-β1 immunoreactivity. No staining was seen in non-transgenic brains (a, arrows point to blood vessel), and no vascular immunoreactivity was detected in AD brains without cerebral amyloid angiopathy. These findings suggest for the first time, that TGF-β1 may play a specific causal role in the development of cerebrovascular amyloid deposition in AD.

Example 2

Production of hAPP Transgenic Animals and Characterization

Human APP transgenic mice were generated with the PDGF-hAPP transgene (Rockenstein et al. (1995) *J. Biol.*

Chem. 270:28257–28267) that induces robust AD-like neuropathology when expressed at high levels in the central nervous system of transgenic mice (Games et al. (1995) Nature 373:523–527; Johnson-Wood et al. (1997) Proc Natl. Acad. Sci. USA 4:1550–5).

Figure 3:
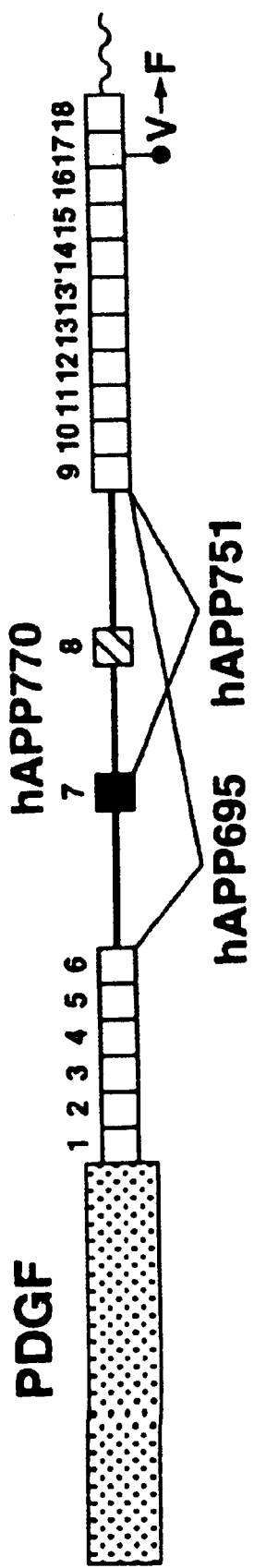
FIG. 3 is a map of the APP construct (PDGF-APP) minigene used to generate APP transgenic animals.

The PDGF-driven hAPP minigene, shown in FIG. 3, represents a fusion product of (from 5' to 3'): (I) hAPP cDNA spanning exon 1 through the XcmI site in exon 6 including 180 bp of exon 6; (ii) a 166 bp PCR-generated fragment of genomic hAPP sequence extending from the XcmI site in exon 6 to an engineered BamHI site in intron 6 (introduced just downstream of position 143 of intron 6 using PCR primer modification); (iii) a 6.8 kb BamHI fragment of hAPP genomic DNA (obtained from a human placental genomic library via λ phage cloning) containing exons 7 and 8 and extending from the BamHI site located 1658 bp upstream of exon 7 to the first BamHI site of intron 8 (the latter BamHI site being located approximately 2329 bp downstream of exon 8); (iv) a 313 bp PCR-generated fragment of genomic hAPP sequence extending from an engineered BamHI site (introduced just upstream of the last 263 bp of intron 8 by PCR primer modification) to the XhoI site in exon 9; and (v) hAPP cDNA sequence extending from the XhoI site in exon 9 to 135 bp downstream of the first hAPP poly(A) signal in the hAPP 3'-untranslated region (UTR). The unique XhoI site in hAPP intron 7 was destroyed using methods well known in the art.

The PDGF-hAPP transgene (Rockenstein et al., (1995) supra) was microinjected into one-cell (C57Bl/6×DBA2) F2 embryos using routine procedures. Twelve transgenic founders were obtained and bred into lines. Cerebral hAPP/Aβ expression levels in the offspring from these lines were determined by RNAse protection assays (Rockenstein et al. (1995), supra), western blot analysis (Games et al., (1995), supra), and an ELISA to detect human and murine Aβ (Johnson-Wood et al. (1997), supra).

The platelet-derived growth factor B chain (PDGF) promoter has previously been shown to drive high-level neuronal expression of an alternatively spliced minigene encoding V717F-mutated (APP770 numbering) hAPP770, hAPP751, and hAPP695 in transgenic mice (Rockenstein et al. (1995) J. Biol. Chem. 270:28257–28267). High expresser hAPP mice produce high levels of human $A\beta_{1-42}$ in the brain and develop prominent AD-type pathology, including typical parenchymal amyloid plaques, in an age- and brain region-dependent manner (Games et al. (1995) Nature 373:523–527; Masliah et al. 1996 J. Neurosci. 16:5795–5811; Johnson-Wood et al. 1997 Proc. Natl. Acad. Sci. USA 94:38. Although some deposition of human Aβ occurs around blood vessels, cerebrovascular amyloidosis is not a prominent feature of this model, and it takes 6–8 months for heterozygous high expresser hAPP mice to develop clear amyloid deposition.

Example 3

Production and Characterization of hAPP/TGF-β1 Bigenic Animals

To assess further the ability of TGF-β1 to promote Aβ deposition in vivo, bigenic mice were generated by crossing HAPP transgenic mice with TGF-β1 transgenic mice. The hAPP transgenic animal selected for the cross was a high expresser hAPP line (H6), which showed slightly higher levels of cerebral hAPP mRNA expression and Aβ production than the previously described (Games et al., (1995), supra) line 109 as determined by ELISA from whole brain homogenates from 4- to 8-week-old mice (line H6=51 ng Aβ/g tissue, line 109=39 ng Aβ/g tissue). The TGF-β1 transgenic animal selected for the cross was a heterozygous TGF-β1 mouse from the lower-expresser line 64. The resulting hAPP/TGF-β1 bigenic mouse was heterozygous for both the hAPP and TGF-β1 transgenes. Singly transgenic littermates (i.e., animals transgenic for either hAPP or TGF-β1) served as controls. Sections from bigenic mice as well as control mice were analyzed for amyloid deposition by both thioflavin S staining and Aβ antibody staining as described above. Antibody stained sections were developed with a fluorescein-labeled secondary antibody.

Figure 4:
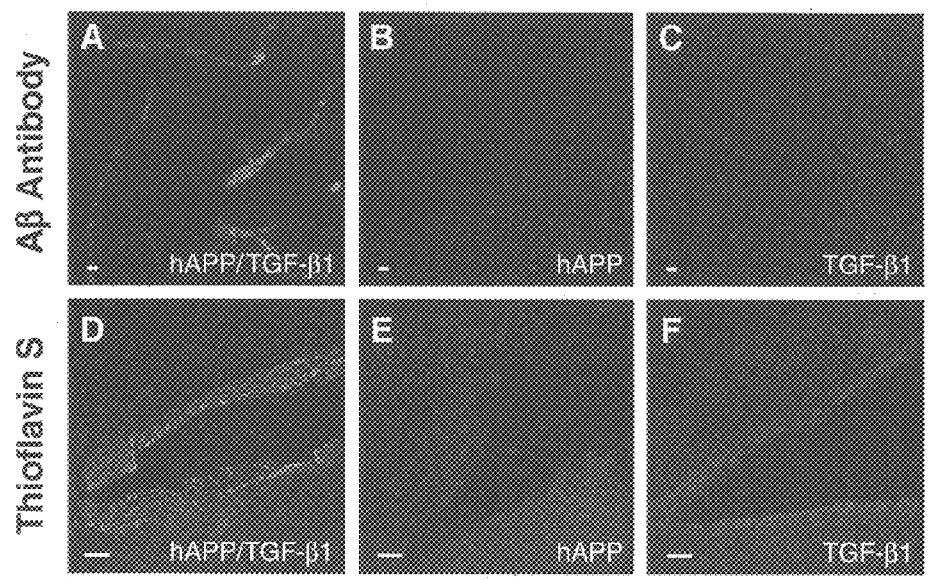
FIG. 4 is panel of photographs of sagittal brain sections of 10-week-old bigenic hAPP/TGF-β1 mice (left top and left bottom panels), as well as control singly transgenic hAPP mice (center top and center bottom panels) and TGF-β1 mice (top right and bottom right panels), stained with either an anti-A$\beta_{1-5}$ antibody 3D6 (top panels) or thioflavin S (bottom panels). Scale bar size is 10 μm.

Co-expression of TGF-β1 and hAPP/Aβ in bigenic mice resulted in cerebrovascular amyloid deposition at 2–3 months of age, whereas singly transgenic littermate controls representing either of the parental genotypes showed no such deposits at this age (FIG. 4). Brains from hAPP/TGF-β1 bigenic mice showed prominent vascular Aβ immunoreactivity (top left panel, cortical blood vessels) and stained with thioflavin S (bottom left panel, meninges of frontal cortex and olfactory bulb). In contrast, there was no or only faint staining with antibody (top center and top right panels) or thioflavin S (bottom center and bottom right panels) of corresponding brain sections from hAPP (top center and bottom center panels) or TGF-β1 (top right and bottom right panels) singly transgenic littermate control mice. The early amyloid deposits in bigenic mice stained with thioflavin S as well as with three of three anti-Aβ antibodies tested (staining with antibodies 10D5 and 2G3 not shown), including Aβ antibody 3D6 (FIG. 4) which failed to label murine amyloid in aged TGF-β1 singly transgenic mice. These data indicate that TGF-β1 promotes or induces the deposition of human Aβ in vivo.

Example 4

Comparison of Bigenic Animal Pathology and Human AD Pathology

To explore further the potential pathogenetic link between TGF-β1 overproduction and AD development, TGF-β1 mRNA levels in frontal cortex with cerebral amyloid angiopathy scores in cohorts of AD patients and normal human controls were compared. Frontal cortex was chosen because this brain region typically develops prominent amyloid deposits in AD. Total RNA was isolated from snap-frozen blocks of postmortem tissue obtained from the frontal cortex of AD cases and controls using TRI Reagent (Molecular Research Center, Cincinnati, Ohio). The quality of total RNA extracted from these tissues was assessed by electrophoretic separation on 1% agarose/formaldehyde gels and densitometric comparison of 28S and 18S ribosomal RNA bands as described (Rockenstein et al. (1995), supra). Only samples with 28S to 18S ratios of 0.8–1 were used for further analysis.

Levels of TGF-β1 mRNA were determined by solution hybridization RNAse protection assays (RPAS) as described (Wyss-Coray et al. (1995), supra) using the following $^{32}$P-labeled antisense riboprobes [protected sequences in brackets]: TGF-β1 probe [nucleotides 999–412 of porcine TGF-β1 cDNA (GenBank accession no M23703)]; β-actin probe [nucleotides 480–559 of mouse β-actin cDNA (GenBank accession no M18194)]. The TGF-β1 riboprobe protects a 280- and a 125-nucleotide fragment of human TGF-β1 mRNA [nucleotides 935–1215 and 1226–1351 of human TGF-β1 cDNA (GenBank accession no X02812)], but does not protect human TGF-β2 or human TGF-β3 transcripts. RNA (10 μg) hybridized to $^{32}$P-labeled antisense riboprobes was digested with 600 U/ml RNase TI (Life Technologies Inc., Gaithersburg, Md.) plus 0.2 µg/ml RNase A (Sigma, St. Louis, Mo.) in 100 µl digestion buffer followed by protein digestion with 10 mg/ml proteinase K (Sigma) (Wyss-Coray et al., supra). Subsequently, RNA was isolated with 4 M guanidine thiocyanate and precipitated in isopropanol.

Samples were separated on 5% acrylarmide/8 M urea Tris-borate-EDTA gels, and dried gels were exposed to Biomax film (Kodak, Rochester, N.Y.). Levels of specific transcripts were compared by quantitating probe- specific signals with a phosphorimager (FUJI-BasHI, Fuji Photo Film Co., Tokyo, Japan) and actin signals were used to correct for differences in RNA content/loading as described (Rockenstein et al. (1995), supra).

Figure 5:
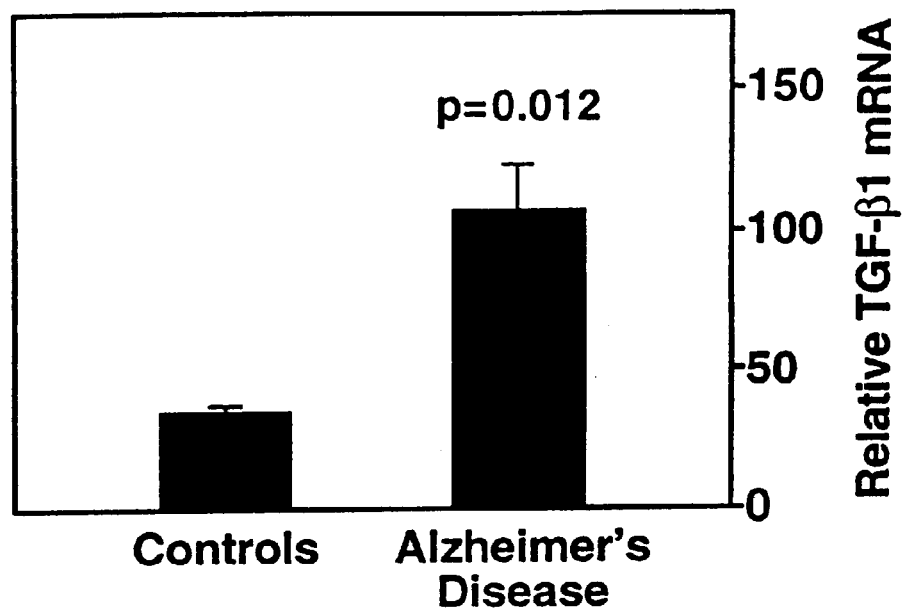
FIG. 5 is a graph showing relative levels of TGF-β1-encoding mRNA in frontal cortex samples from normal controls and individuals having AD.
Figure 6:
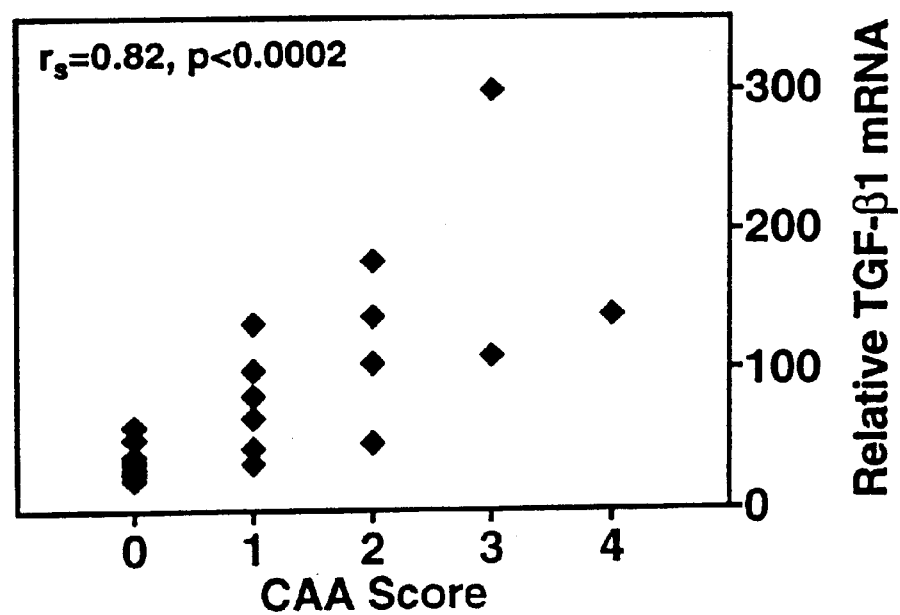
FIG. 6 is a graph showing simple regression analysis of TGF-β1 mRNA levels and cerebral amyloid angiopathy (CAA) scores from the experiment in FIG. 5.

Significantly higher TGF-β1 mRNA levels were found in AD cases (n=15; Blessed score≧10) than in non-demented controls (n=7; Blessed score=0) by Mann-Whitney's unpaired two-tailed U test. Specifically, AD cases (with or without cerebral amyloid angiopathy) had threefold higher TGF-β1 mRNA levels than non-demented controls (FIG. 5). In addition, simple regression analysis of TGF-β1 mRNA levels and cerebral amyloid angiopathy (CAA) scores from the above patient group revealed a strong positive correlation between TGF-β1 mRNA levels and cerebral amyloid angiopathy scores (FIG. 6; correlation coefficient r=0.74, p, 0.0001), but not with the number of amyloid plaques r=0.426). A weak correlation between TGF-β1 mRNA levels and the number of tangles was observed r=0.504, p 0.03).

These data demonstrate for the first time that chronic glial overexpression of TGF-β1 results in time- and dose-dependent development of thioflavin S-positive, Aβ-immunoreactive cerebrovascular and meningeal amyloid deposits in vivo. Without being held to theory, it is possible that TGF-β1 promotes or mediates the deposition of amyloid in the central nervous system indirectly through its capacity to induce Aβ-binding extracellular matrix proteins (Finch et al. (1993) *J. Cell. Biochem.* 53:314–322; Wyss-Coray et al. (1995), supra) as well as apolipoprotein E, which may function as seeds or chaperones for amyloid deposition (Fillit et al. (1995) *Lab. Invest.* 72:249–253; Wisniewski et al. (1992) *Acta Neuropathol.* 84:11–127; Schmechel et al. (1993) *Proc. Natl. Acad. Sci. USA* 90:9649–9653). These findings strongly suggest that overexpression of TGF-β1 plays a critical regulatory role in AD-related amyloidogenesis.

What is claimed is:

1. A transgenic mouse comprising stably integrated into the genome of said mouse a first transgenic nucleotide sequence encoding bioactive transforming growth factor-β1 (TGF-β1) operably linked to a promoter and a second transgenic nucleotide sequence encoding a human amyloid precursor protein (hAPP) operably linked to a promoter, wherein said first and said second transgenic nucleotide sequences are expressed, and wherein, as a result of said expression, said transgenic mouse develops, within about three months of age, cerebrovascular amyloid deposits associated with a disease selected from the group consisting of Alzheimer's disease (AD) and cerebral amyloid angiopathy (CAA).

2. The mouse of claim 1, wherein the mouse is heterozygous for a human amyloid precursor protein (hAPP) gene product.

3. The mouse of claim 1, wherein the mouse is homozygous for a human amyloid precursor protein (hAPP) gene product.

4. The mouse of claim 1, wherein the transgenic nucleotide sequence encoding bioactive TGF-β1 is overexpressed, resulting in elevated levels of TGF-β1 relative to a normal mouse of the same strain.

5. The transgenic mouse of claim 1, wherein said hAPP is APP770.

6. The transgenic mouse of claim 1, wherein said hAPP is APP751.

7. The transgenic mouse of claim 1, wherein said hAPP is APP695.

8. The transgenic mouse of claim 1, wherein said hAPP is a mutant hAPP.

9. The transgenic mouse of claim 8, wherein said mutant hAPP comprises a familialAD mutation.

10. The transgenic mouse of claim 8, wherein said hAPP mutant is APP695 comprising a valine to isoleucine substitution at amino acid 642.

11. The transgenic mouse of claim 8, wherein said hAPP mutant is APP695 comprising a valine to phenylalanine substitution at amino acid 642.

12. The transgenic mouse of claim 8, wherein said hAPP mutant is APP695 comprising a valine to glycine substitution at amino acid 642.

13. A method of screening for biologically active agents that modulate a phenomenon associated with Alzheimer's disease (AD), the method comprising:

combining a candidate agent with a transgenic mouse comprising a transgenic nucleotide sequence encoding bioactive transforming growth factor-β1 (TGF-β1) operably linked to a promoter and stably integrated into the genome of said mouse, wherein said nucleotide sequence is expressed and wherein said expression results in cerebrovascular amyloid deposits associated with AD; and determining the effect of said agent upon a phenomenon associated with AD.

14. The method of claim 13, wherein the transgenic mouse further comprises a second transgenic nucleotide sequence encoding a human amyloid precursor protein (hAPP) gene product, wherein said second nucleotide sequence is expressed and wherein expression of said second nucleotide sequence results in development, within about three months of age, of cerebrovascular amyloid deposits associated with AD in said mouse.

15. The method of claim 13, wherein the phenomenon associated with Alzheimer's disease is amyloid deposition.

16. The method of claim 13, wherein the phenomenon associated with Alzheimer's disease is production of a proteolytic fragment of hAPP selected from the group consisting of $A\beta_{1-40}$ and $A\beta_{1-42}$.

17. The method of claim 13, wherein the phenomenon associated with Alzheimer's disease is neuronal cell loss.

18. A method of screening for biologically active agents that modulate a phenomenon associated with cerebral amyloid angiopathy (CAA), the method comprising:

combining a candidate agent with a transgenic mouse comprising a transgenic nucleotide sequence encoding bioactive transforming growth factor-β1 (TGF-β1) operably linked to a promoter and stably integrated into the genome of said mouse, wherein said nucleotide sequence is expressed and wherein said expression results in cerebrovascular amyloid deposits associated with CAA; and determining the effect of said agent upon a phenomenon associated with CAA.

19. The method of claim 18, wherein the transgenic mouse further comprises a second transgenic nucleotide sequence encoding a human amyloid precursor protein (hAPP) gene product stably integrated into the genome of said mouse, wherein said second nucleotide sequence is expressed and wherein said animal develops, within about three months of age, cerebrovascular amyloid deposits associated with CAA.

20. The method of claim 16, wherein the phenomenon associated with cerebral amyloid angiopathy is cerebrovascular amyloid deposition.

21. The method of claim 16, wherein the phenomenon associated with cerebral amyloid angiopathy is cerebral hemorrrhage.

22. A method of screening for biologically active agents that modulate a pathology associated with Alzheimer's disease (AD), the method comprising:

combining a candidate agent with a transgenic mouse comprising stably integrated into the genome of said mouse a first transgenic nucleotide sequence encoding bioactive transforming growth factor-$\beta$1 (TGF-$\beta$1) operably linked to a promoter and a second transgenic nucleotide sequence encoding a human amyloid precursor protein (hAPP) operably linked to a promoter, wherein said first and said second transgenic nucleotide sequences are expressed, and wherein, as a result of said expression, said transgenic animal develops, within about three months of age, cerebrovascular amyloid deposits associated with AD; and determining the effect of said agent upon a pathology associated with AD.

23. A method of screening for biologically active agents that modulate a pathology associated with cerebral amyloid angiopathy (CAA), the method comprising:

combining a candidate agent with a transgenic mouse comprising stably integrated into the genome of said mouse a first transgenic nucleotide sequence encoding bioactive transforming growth factor-$\beta$1 (TGF-$\beta$1) operably linked to a promoter and a second transgenic nucleotide sequence encoding a human amyloid precursor protein (hAPP) operably linked to a promoter, wherein said first and said second transgenic nucleotide sequences are expressed, and wherein, as a result of said expression, said transgenic mouse develops, within about three months of age, cerebrovascular amyloid deposits associated with CAA; and determining the effect of said agent upon a pathology associated with CAA.

* * * * *

UNITED STATES PATENT AND TRADEMARK OFFICE
CERTIFICATE OF CORRECTION

PATENT NO.   : 6,175,057 B1
DATED        : January 16, 2001
INVENTOR(S)  : Mucke, et al.

It is certified that error appears in the above-identified patent and that said Letters Patent is hereby corrected as shown below:

Following the first paragraph of the specification please insert a second paragraph which reads:

"This invention was made with Government support under Grant Nos. AG05131, AG10689 and AG11385, awarded by the National Institutes of Health. The Government has certain rights in this nvention."

Signed and Sealed this

Twenty-fifth Day of September, 2001

Attest:

*Nicholas P. Godici*

NICHOLAS P. GODICI
*Attesting Officer*    *Acting Director of the United States Patent and Trademark Office*